(12) United States Patent
Serafin, Jr.

(10) Patent No.: US 8,834,576 B1
(45) Date of Patent: Sep. 16, 2014

(54) CERAMIC WITH METAL/ALLOY COATING

(76) Inventor: Louis A. Serafin, Jr., Burtchville Township, St. Clair County, MI (US)

( * ) Notice: Subject to any disclaimer, the term of this patent is extended or adjusted under 35 U.S.C. 154(b) by 214 days.

(21) Appl. No.: 12/932,480

(22) Filed: Feb. 25, 2011

Related U.S. Application Data (63) Continuation-in-part of application No. 12/584,482, filed on Sep. 4, 2009, which is a continuation-in-part of application No. PCT/US2008/002768, filed on Mar. 1, 2008.

(60) Provisional application No. 60/904,803, filed on Mar. 5, 2007, provisional application No. 60/930,157, filed on May 14, 2007, provisional application No. 60/930,862, filed on May 18, 2007, provisional application No. 61/339,155, filed on Mar. 1, 2010, provisional application No. 61/397,608, filed on Jun. 14, 2010.

(51) Int. Cl.
*A61F 2/02* (2006.01)
*A61F 2/38* (2006.01)
*A61L 27/10* (2006.01)

(52) U.S. Cl.
CPC ....... *A61L 27/10* (2013.01); *A61F 2310/00179* (2013.01); *A61F 2310/00395* (2013.01)
USPC ............. 623/20.32; 623/23.5; 623/23.51; 623/23.53; 623/23.56

(58) Field of Classification Search
USPC .......................................... 623/11.11; 29/6.1
See application file for complete search history.

(56) References Cited

U.S. PATENT DOCUMENTS

| 4,279,655 | A | * | 7/1981 | Garvie et al. ................ 501/20 |
| 4,612,160 | A | * | 9/1986 | Donlevy et al. ................ 419/2 |
| 4,891,341 | A | * | 1/1990 | Cutler et al. ................ 501/89 |
| 5,024,976 | A | * | 6/1991 | Mehrotra et al. ............ 501/89 |
| 5,347,887 | A | * | 9/1994 | Rosenthal et al. .......... 76/104.1 |
| 5,453,227 | A | * | 9/1995 | Rieger ...................... 264/40.1 |
| 5,674,802 | A | * | 10/1997 | Sheppard ................ 502/439 |
| 5,683,761 | A | * | 11/1997 | Bruce et al. ............... 427/596 |
| 6,008,432 | A | * | 12/1999 | Taylor ...................... 623/23.3 |
| 6,398,815 | B1 | * | 6/2002 | Pope et al. ................ 623/23.6 |
| 2002/0198602 | A1 | * | 12/2002 | Nawa et al. .............. 623/23.56 |
| 2006/0025866 | A1 | * | 2/2006 | Serafin et al. ............ 623/23.56 |
| 2008/0195222 | A1 | * | 8/2008 | Rauguth et al. ........... 623/23.6 |
| 2008/0208353 | A1 | * | 8/2008 | Kumar et al. ............ 623/23.56 |
| 2010/0076566 | A1 | * | 3/2010 | Serafin et al. ............ 623/20.32 |

OTHER PUBLICATIONS

Wikipedla, Titanium alloy, http://en.wikipedia.org/wiki/Titanium_alloy, four pages, last modified Oct. 19, 2011 at 07:05.

* cited by examiner

*Primary Examiner* — David H Willse
*Assistant Examiner* — Javier Blanco
(74) *Attorney, Agent, or Firm* — Christopher John Rudy (57) ABSTRACT

Fired magnesium oxide stabilized zirconia ceramic body having a highly smooth, polished or otherwise equivalent surface has, on at least part of the surface, a metal/metal alloy coating. The fired ceramic body can be a magnesium oxide stabilized tetragonally toughened zirconia. The coating can be from a metal or metal alloy other than by tantalum vapor deposition, and can include a titanium metal or alloy. The coated magnesium oxide stabilized zirconia ceramic can be a tool or an orthopedic implant or component for an orthopedic implant, which can be a load bearing implant or component for a load bearing implant having an articular surface and a nonarticular surface where the metal or metal alloy coating is on at least part of the nonarticular surface. Plasma arc spraying under vacuum may be employed.

20 Claims, 7 Drawing Sheets

CERAMIC WITH METAL/ALLOY COATING

This is a continuation-in-part of U.S. patent application Ser. No. 12/584,482 filed on Sep. 4, 2009 A.D., which is a continuation-in-part of PCT/US2008/002768 filed on Mar. 1, 2008 A.D., and which, as does the present matter, claims priority benefits through the international application under the Patent Cooperation Treaty and/or Title 35 United States Code, particularly under sections 119(e), 120, 363 and/or 365, of U.S. provisional patent application Nos. 60/904,803 filed on Mar. 5, 2007 A.D., 60/930,157 filed on May 14, 2007 A.D., and 60/930,862 filed on May 18, 2007 A.D. The '482 U.S. application published as Pub. No. US 2010/0076566 A1, and the '768 PCT application published as WO 2008/109016 A1. This also claims priority benefits under 35 USC 119(e) of U.S. provisional patent application Nos. 61/339,155 filed on Mar. 1, 2010 A.D., and 61/397,608 filed on Jun. 14, 2010 A.D. The specifications of those applications and publications, in their entireties, which of course include their drawings, are incorporated herein by reference.

FIELD AND PURVIEW OF THE INVENTION

This concerns a ceramic such as a magnesium oxide stabilized zirconia, which has a highly smooth or polished surface or the like for coating, coated with a metal or metal alloy. As illustrations, it can be embodied as a tool or a surgical implant, which can be a prosthetic load-bearing implant, say, made with a zirconia ceramic having a porous coating of the metal or alloy. For example, the implant or component can embrace femoral and/or tibial component(s) for a human knee, say, made of a partially stabilized zirconia (PSZ) such as a magnesium oxide stabilized transformation toughened zirconia (MgO-TTZ) coated on a highly smooth or polished surface with a commercially pure titanium (CPT) coating.

BACKGROUND TO THE INVENTION

Certain metal or metal alloy porous coated ceramic materials as prosthetic implants, especially for load bearing, are known. Prior to the '482 U.S. and '768 PCT applications, Serafin, Jr. et al., U.S. patent application Ser. No. 11/657,385, disclosed a metal/alloy on ceramic coating, which has broad applicability, with an exemplary ceramic MgO-TTZ and exemplary physical attachment features including undercut grooves and/or holes. A problem within the foregoing, for example, as disclosed by the parent in its Examples 5 and 6, is that, the coating can be extremely strong and reliable in some cases, but less strong and reliable in others.

It would be desirable to provide such a strong and reliable bond more uniformly.

A FULL DISCLOSURE OF THE INVENTION

In general, provided is a ceramic with metal/alloy coating article comprising a fired magnesium oxide stabilized zirconia ceramic body having a highly smooth, polished or otherwise equivalent surface; and, on at least part of the surface, the metal/metal alloy coating. The fired ceramic body can be an MgO-TTZ. The coating can be from a metal or metal alloy other than by tantalum vapor deposition, and can include a titanium metal or alloy. The article can be a tool or an orthopedic implant or component for an orthopedic implant where the fired ceramic body comprises a body for the implant or component having the aforesaid surface; and, on at least part of the surface, the metal/metal alloy coating. The orthopedic implant or component can be load bearing and have an articular surface and a nonarticular surface, where the porous coating is on at least part of the nonarticular surface. A method to provide the article is provided, say, with plasma arc spraying under vacuum.

The invention is useful in providing metal/metal alloy coatings to ceramic manufactures. It can be useful as an implant in the field of orthopedics.

Significantly, by the invention, the art is advanced in kind. Not only is a magnesium oxide stabilized zirconia ceramic body coated with a metal or metal alloy, but extraordinary holding power of the coating to the ceramic body can be provided. And, not only that, but also the extraordinary holding power of the ceramic and metal/metal alloy is provided with high reliability. In other words, a zirconia ceramic sample set coated with the metal/metal alloy can have nearly all, if not all, of its population characterized by the extraordinary holding power. No binder need be employed. Thus, for instance, magnesium oxide stabilized zirconia ceramic bodies such as for tools, or prosthetic implants or implant components, especially those made with an MgO-TTZ ceramic, and notably those which are load bearing, can be provided with a reliable titanium or titanium alloy porous coating, for example, CPT, which may be subjected to nitric acid treatment for forming a nitride. And so, technicians and surgeons can have a highly reliable tool or implant system, with the latter, in addition to reliability, able to ameliorate if not avoid allergic reaction to standard metal implants such as in patients allergic to the nickel of a conventional cobalt-chrome femoral component for a knee. The invention is efficient in manufacture, and, since forming grooves or holes, grit-blasting and so forth can be avoided, processing steps can be reduced, further efficiencies in manufacture are provided. Numerous further advantages attend the invention.

The drawings form part of the specification hereof. With respect to the drawings, which are not necessarily drawn to scale, the following is briefly noted:

FIGS. 1-8 show a femoral implant bicompartmental component for a human cruciate-retaining knee joint implant, a type of a component for a non-rotating hinge knee implant, for example, made with MgO-TTZ. FIGS. 1-3 are views of the component without coating, with FIG. 1 a rear, top perspective view; FIG. 3 a top view. FIGS. 4-8 are views of the ceramic component of FIGS. 1-3 coated, for example, with a CPT porous coating, with FIG. 4 a top view.

FIGS. 9-16 depict a tibial tray implant component for a tibial portion of a human knee joint, for example, made with MgO-TTZ. FIGS. 9-11 are views of the component without coating, with FIG. 9 a bottom view; FIGS. 12-16 are views are of the ceramic component of FIGS. 9-11 coated, for example, with a CPT porous coating, with FIG. 12 a top view.

FIG. 17 is a view of a tool of an MgO-TTZ coated with CPT that is later machined.

FIGS. 18-27 depict other exemplary embodiments of the invention, to wit:

FIGS. 18 and 19 are perspective views of cups for some enarthrodial joint implants, with FIG. 18 an acetabular cup; and FIG. 19 a glenoid cup.

FIG. 20 is top plan view of a great toe implant.

FIG. 21 is a side plan view of a temporal mandibular joint

FIG. 22 is a rear, perspective view of a unicompartmental femoral component condylar implant FIG. 23 is a "top," perspective view of a patellofemoral implant.

FIGS. 24-27 are views of an ankle implant or ensemble, with FIG. 24 a side plan view of a talus cap, which may be employed by itself as a hemi-implant; FIG. 25 a front plan view of the talus cap of FIG. 24; FIG. 26 a side plan view of a tibial tray that may be used with a talus cap as of FIG. 24; and FIG. 27 a front plan view of the tibial tray of FIG. 26.

The invention can be further understood by the detail set forth below, which may be read in view of the drawings. As with the foregoing, the following is to be understood in an illustrative and not necessarily limiting sense.

The present coated ceramic embraces a fired magnesium oxide stabilized zirconia ceramic body, which has a highly smooth, polished or otherwise equivalent surface and generally serves as a substrate. The coated, finished product can be a tool or other item, which may be a surgically implantable implant or component thereof, which may be for a human patient. The implant can be intended for a load bearing application. Highly smooth, polished or otherwise equivalent surface(s) of the ceramic such as those surfaces that can be characterized as having a suitable micro-finish smoothness are coated with the metal or metal alloy to provide the extremely strong, highly reliable coating.

The ceramic can be a magnesium oxide stabilized zirconia ceramic, which, in one embodiment, is a magnesium oxide stabilized PSZ ceramic such as an MgO-TTZ ceramic. See, e.g., Serafin et al., Pub. No. US 2006/0025866 A1 and WO 2004/0830340 A2 and A3. Accordingly, before application of the porous coating, the ceramic body can be prepared by a method as found therein or as otherwise known and/or practiced in the art. The MgO-TTZ ceramic can conform to ASTM F 2393-04, "Standard Specification for High-Purity Dense Magnesia Partially Stabilized Zirconia (Mg-PSZ) for Surgical Implant Applications."

Polishing of surface(s), if necessary, precedes coating, or the fired surface(s) may have or otherwise be provided with the highly smooth, polished or otherwise equivalent surface(s), which may be characterized as polished or polish-like. Harperizing vibrational and rotational polishing, vibrational polishing, and so forth may be employed. For example, such polishing may be carried out with diamond dust suspended in oil.

A polished or polish-like surface, for example, an about from 1-Ra to 2-Ra finish in micro-inch (0.025 mm) units, or a more smooth surface finish, say, an about from 0.5-Ra to 1.5-Ra finish or more smooth surface finish, to include an about 1-Ra finish, as may be found on a polished condyle of an MgO-TTZ femoral knee implant, may be employed and provided with the metal or metal alloy coating. Rougher surfaces can engender less high reliability and strength in coating It is contemplated, without necessarily wishing to be bound thereby, that the extraordinarily strong and highly reliable bond is formed with diffusion bonding or the like.

Any suitable metal or metal alloy can be employed as the coating. The coating may be titanium metal or an alloy with titanium. The coating can be CPT. Note, ASTM F-67.

For example, CPT can be sprayed by a plasma arc under vacuum, but with the metal powder being carried by argon pick-up gas through a robotic sprayer, to be met with a flow of hydrogen gas to enhance the heat of the spray, which mixture is carried through the plasma arc of the sprayer, and onto the surface that is to be coated. The sprayer also can deliver argon gas, say, from jet spray openings spaced laterally from the central spray with the metal, so that the argon is directed to the surface so as to cool the ceramic as soon as the liquid metal hits the ceramic.

The metal or metal alloy coating can be provided to any suitable extent or thickness. As an illustration, in an orthopedic implant, for example, femoral and tibial tray components to a human knee joint implant, or to the outside of cups of an enarthrodial joint implant, a CPT porous coating can be applied to a thickness about from 0.015 to 0.025 of an inch (about from 0.038 to 0.064 cm) with an about 100-micron to about 300-micron pore size.

The metal/alloy coating may be applied in layers. An initial coating layer may be applied, optionally then cooled, before applying subsequent layer(s) of metal/alloy coating.

The metal/alloy coating may be applied as one substantially uniform sample of metal or alloy. It may be applied as two or more samples of metal or alloy, say, by varying the metal/alloy composition during uninterrupted application or by providing the metal or alloy as differing layers.

Extraordinary holding power of the metal/metal alloy coating to the magnesium oxide stabilized zirconia ceramic body can be provided with high reliability to all or nearly all the items in a lot that is manufactured hereby. For instance, the metal or metal alloy coating may resist being pulled or sheared off the magnesium oxide stabilized zirconia ceramic body to a value of about 2,000 pounds (about 0.91 metric tons) or more of force, to include about 3,000 pounds (about 1.4 metric tons) or more of force, or about 4,000 pounds (about 1.8 metric tons) or more of force, or about 5,000; 6,000; 7,000; 8,000; 9,000 or even 10,000 pounds (about 2.3; 2.7; 3.2; 3.6; 4.1 or even 4.5 metric tons) or more of force. Compare, ASTM F-1044-05, ASTM F-1160-98 and ASTM F-1659-95. Many of such values meet or exceed United States Food and Drug Administration (USFDA) requirements for metal or metal alloy porous coatings on metal or metal alloy implants.

With more particular reference to the drawings, magnesium oxide stabilized zirconia ceramic with metal/alloy coating as implant 1000 can be embodied as a load bearing prosthetic implant or component therefor. The implant 1000 may be made of MgO-TTZ with a titanium plasma spray (TPS) CPT porous coating, and it may be modular.

The implant 1000 generally has magnesium oxide stabilized zirconia ceramic body 1, articular surface 2, receiving surface 3 for receiving the metal or metal alloy coating, which is polished or polish-like, and metal/metal alloy porous coating 4. The articular surface 2 is generally smooth, and may be polished, as part of the magnesium oxide stabilized zirconia ceramic body. In other words, the articular surface can be generally provided as a highly smooth, polished or otherwise equivalent surface of the magnesium oxide stabilized zirconia ceramic body 1. However, an articular surface may be of a material other than the magnesium oxide stabilized zirconia ceramic body 1 such as by being a coated metal or metal alloy on the magnesium oxide stabilized zirconia ceramic body, which coated metal or alloy on the magnesium oxide stabilized zirconia ceramic body substrate is made to be smooth and suitable for the articulation under consideration. An articular surface 2' may also be made as an insert that may be attached to the magnesium oxide stabilized zirconia ceramic body such as being a polyethylene insert as a liner for a metal/metal alloy coated magnesium oxide stabilized zirconia ceramic tibial tray, or as a liner with dovetail ridge(s) that slide into corresponding undercut groove(s) in an appropriate surface of the magnesium oxide stabilized zirconia ceramic body. Depending on the configuration and application of the implant 1000 with its magnesium oxide stabilized zirconia ceramic body 1 and articular surface 2, 2', in general, the receiving surface 3 can be provided at, and the metal/metal alloy porous coating 4 can be applied on the receiving surface 3 to, any suitable location of the magnesium oxide stabilized zirconia ceramic body 1. Thus, for example, diamond dust polishing of inner surfaces of "box" geometry of an MgO-TTZ femoral knee implant component 100, which forms the receiving surface 3, on which the metal/metal alloy coating 4, say, CPT, may be applied thereto, say, by TPS, to a thickness of about from 0.015 to 0.025 inch (about from 0.038 to 0.064 cm); or diamond dust polishing the underside of a tibial tray of a knee joint tibial component 200 made of MgO-TTZ can provide the receiving surface 3, on which a CPT coating 4 may be applied by TPS to the same or similar thickness as the femoral component 100.

Figure 1:
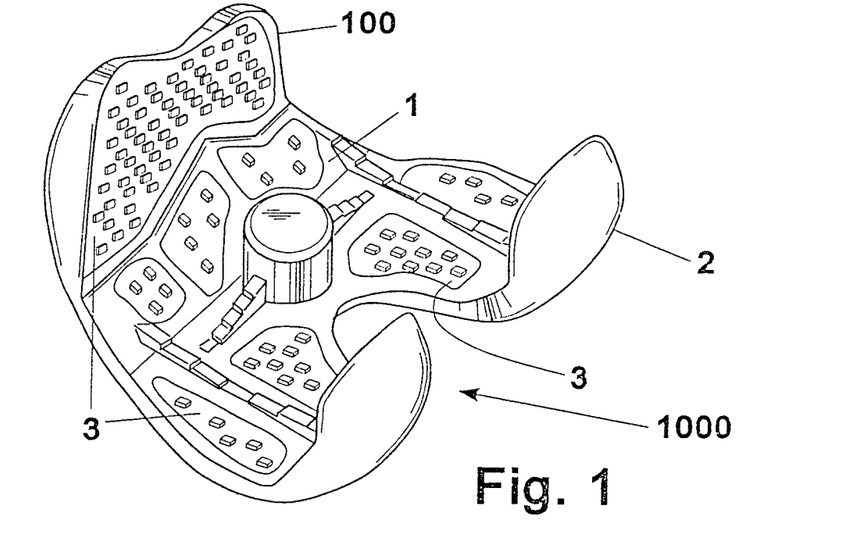
Figure 2:
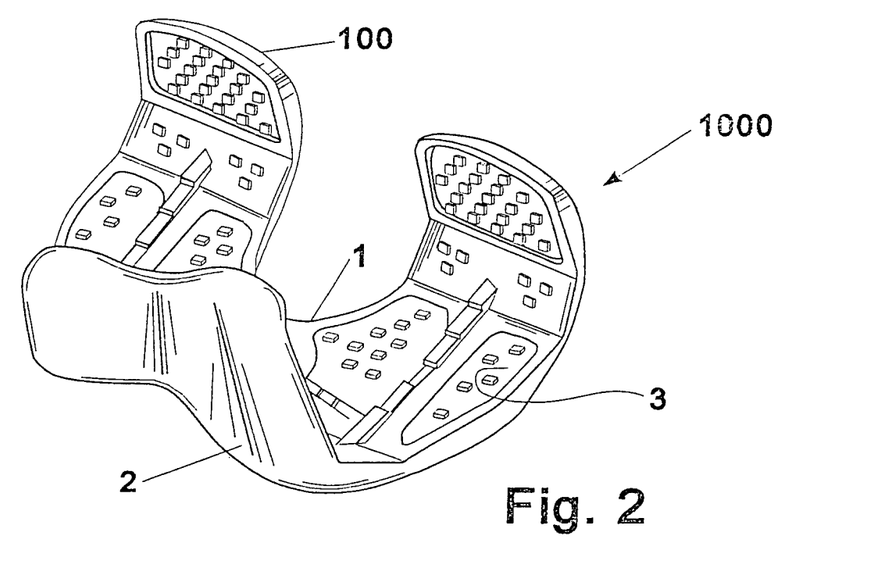
FIG. 2 a front, top perspective view.
Figure 3:
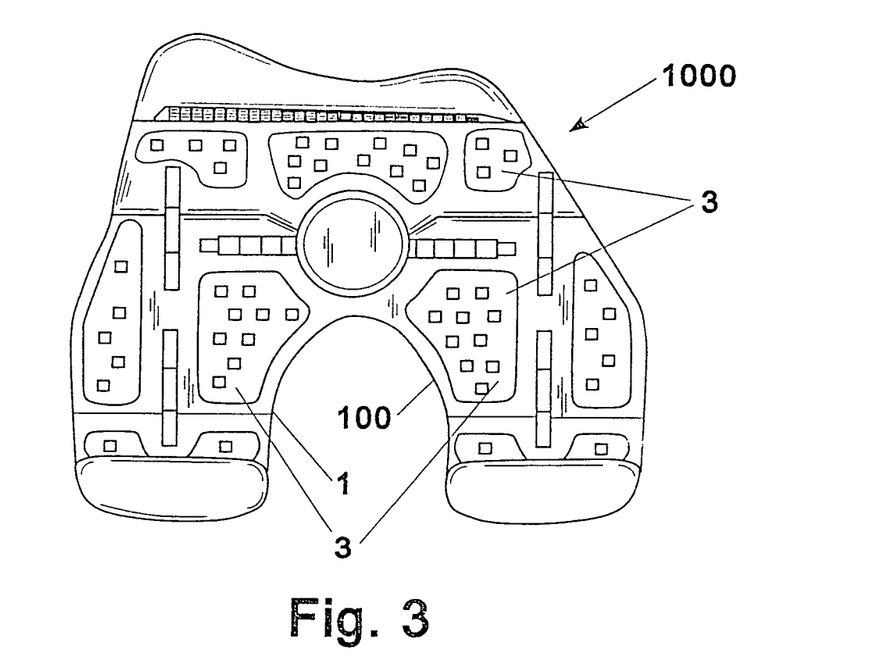
Figure 4:
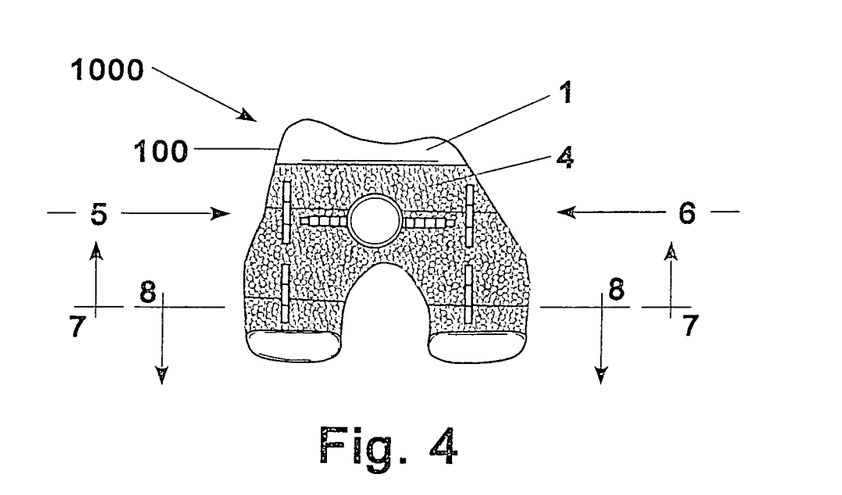
Figure 5:
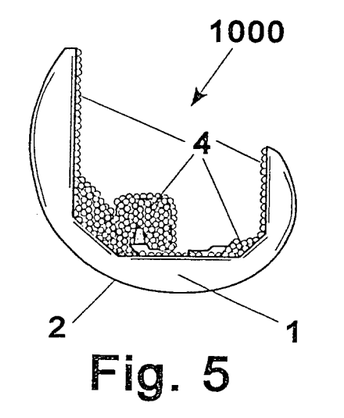
FIG. 5 a side view taken along arrow 5 in FIG. 4.
Figure 6:
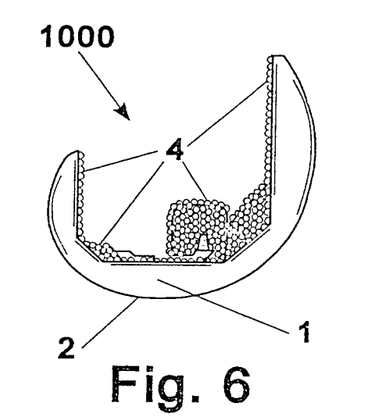
FIG. 6 a side view taken along arrow 6 in FIG. 4.
Figure 7:
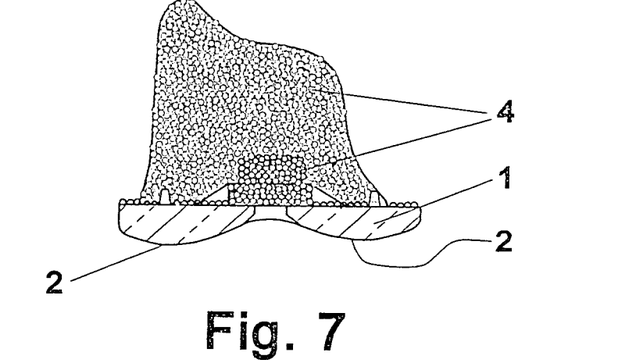
FIG. 7 a sectional view taken in the direction of 7-7 in FIG. 4.
Figure 8:
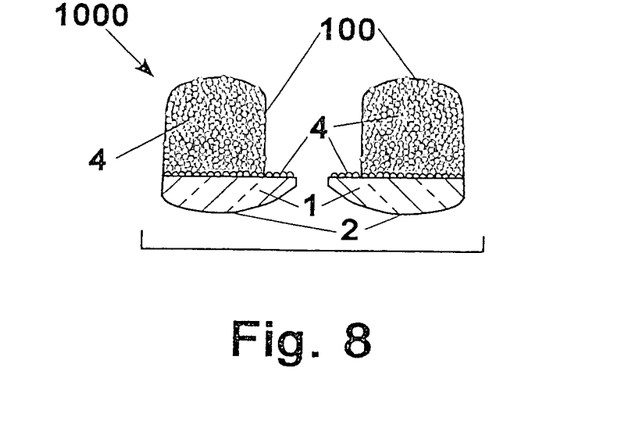
FIG. 8 a sectional view taken in the direction of 8-8 in FIG. 4.
Figure 9:
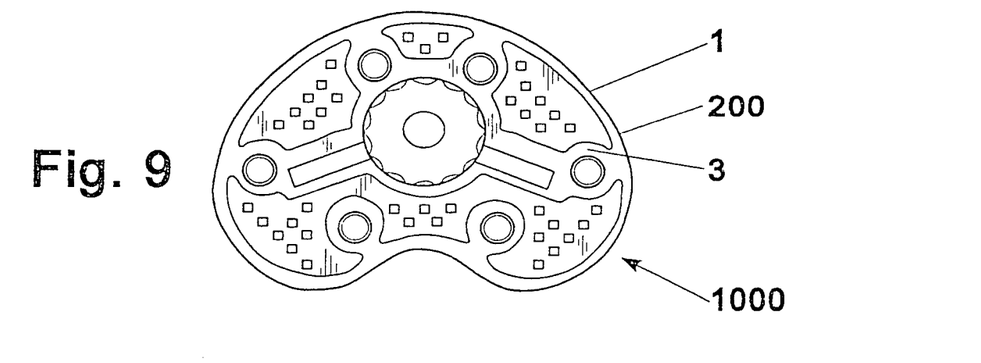
Figure 10:
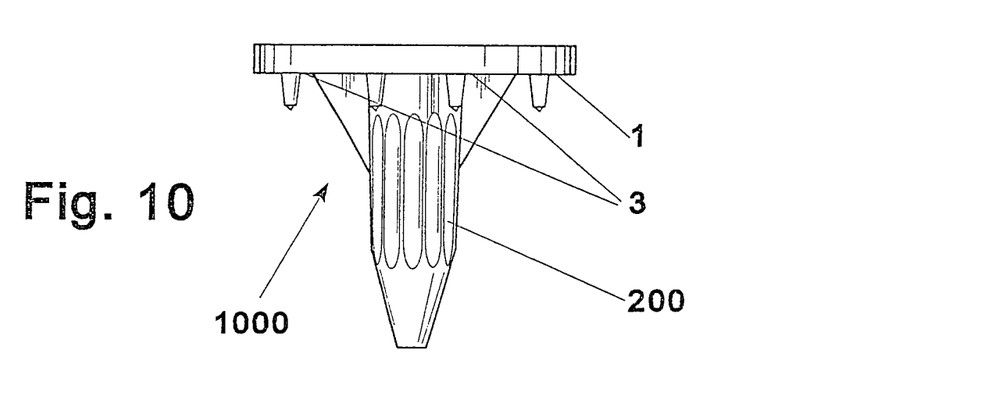
FIG. 10 a side view.
Figure 11:
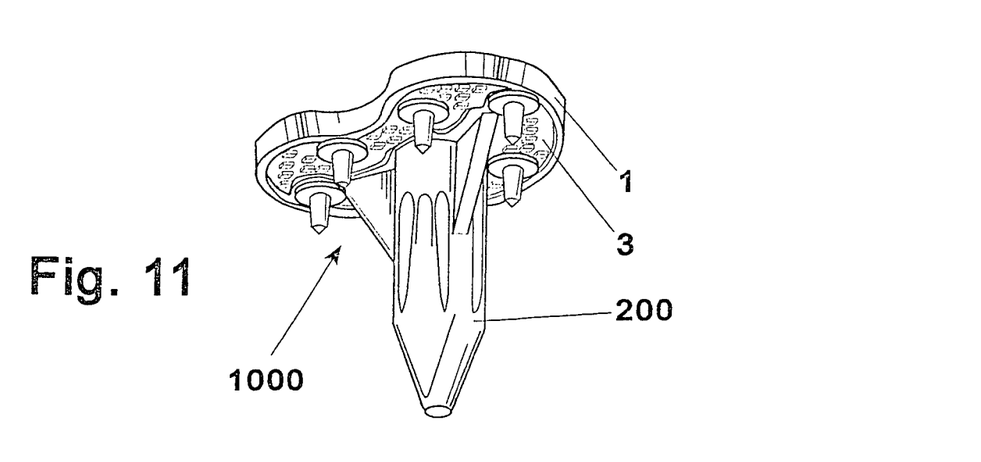
FIG. 11 a bottom perspective view.
Figure 12:
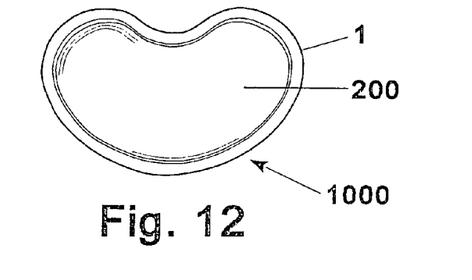
Figure 13:
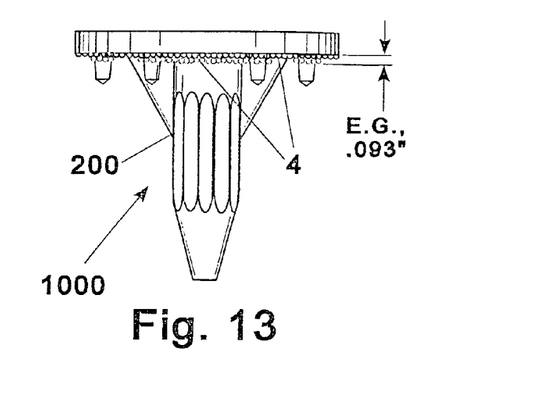
FIG. 13 a side view in elevation.
Figure 14:
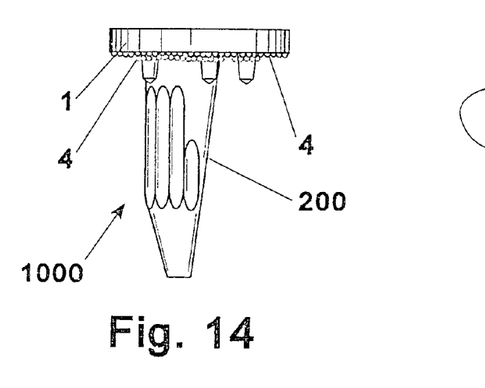
FIG. 14 a side view in elevation at a 90-degree angle to that of FIG. 13.
Figure 15:
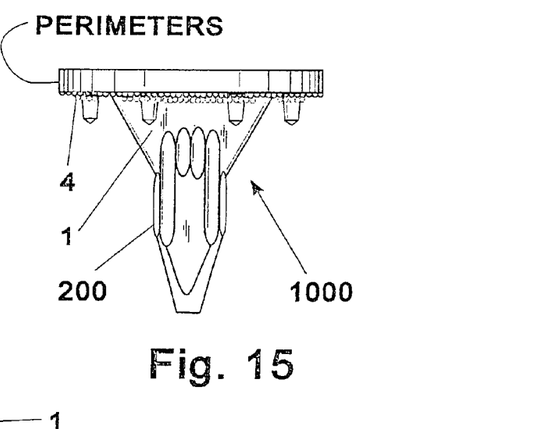
FIG. 15 a side view in elevation at a 180-degree angle to that of FIG. 13.
Figure 16:
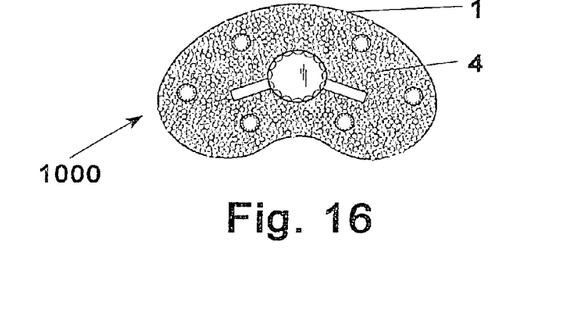
FIG. 16 a bottom view.
Figures 17, 18, 19, 20, 21, 22, 23, 24, 25, 26, 27:
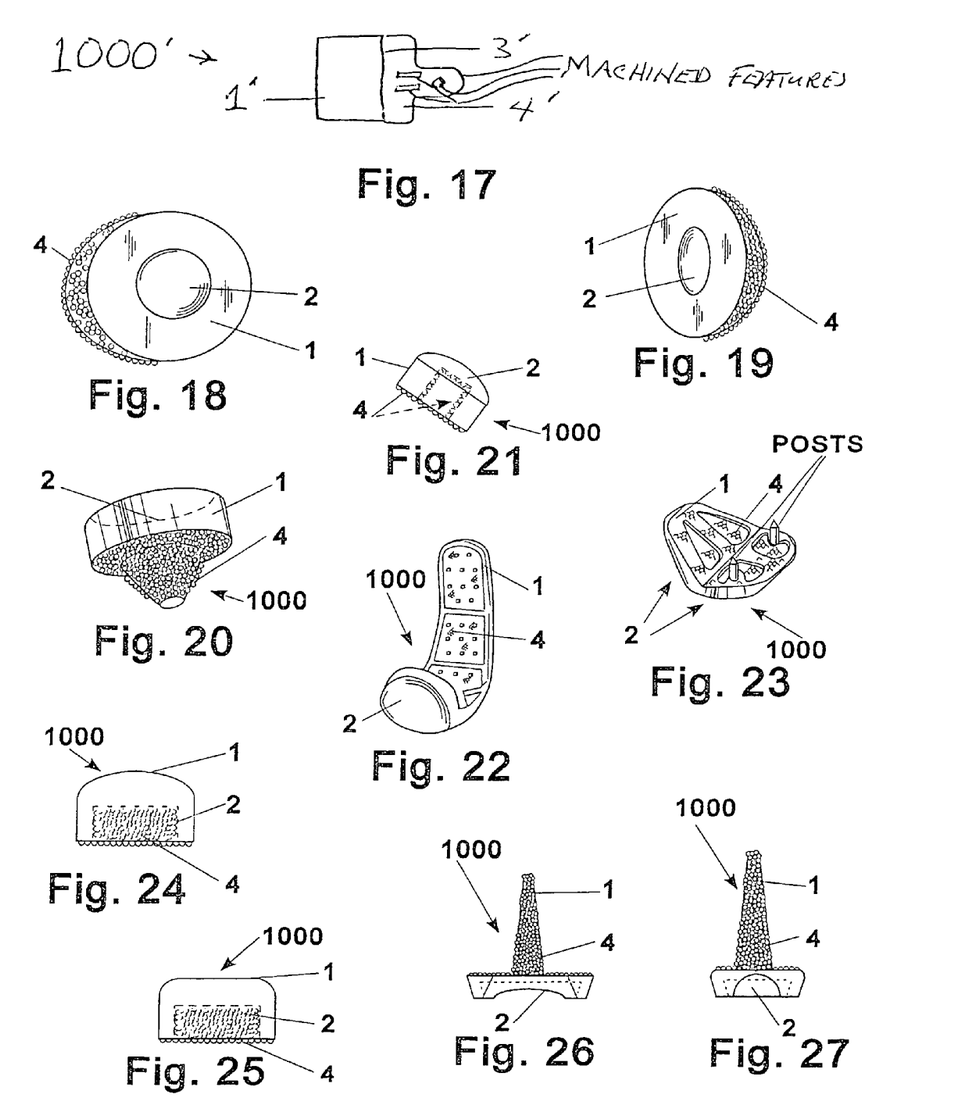

Magnesium oxide stabilized zirconia ceramic with metal/alloy coating as tool 1000' includes magnesium oxide stabilized zirconia ceramic body 1'; receiving surface 3' for receiving the metal or metal alloy coating, which is polished or polish-like; and metal/metal alloy coating 4'. Either the magnesium oxide stabilized zirconia ceramic body 1' or the metal/alloy coating 4', or both, can be provided with a tool working surface or other features such as machined hole, groove, cutting tip, and so forth and the like.

The following examples further illustrate the invention:

EXAMPLE 1

Figure 28:
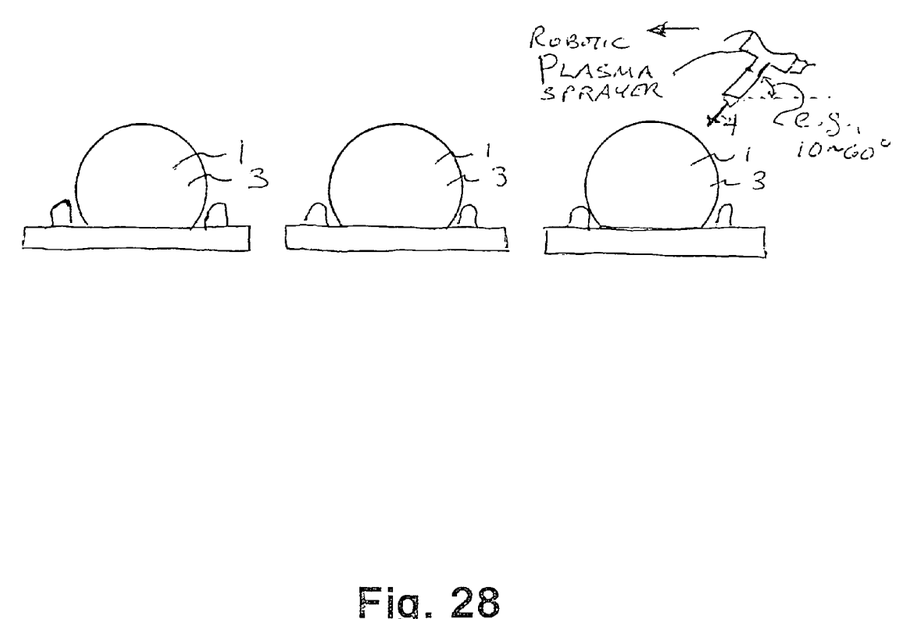
FIG. 28 depicts manufacture of ceramics with metal/alloy coating.

CPT-coated ceramic specimens are prepared and tested as follows:

Polished ceramic femoral head balls for total hip joint prostheses, as noted below, are placed on holding trays in a plasma spraying device. A TPS porous coating with CPT is uniformly sprayed onto the balls. Spraying is done robotically under an Argon atmosphere, following removal of air with a vacuum followed by purging with Argon gas, with Argon gas from the nozzle about from 60~100 psi pressure. Compare, FIG. 28. The coated balls are removed from the device and inspected. The following observations are made:
Ceramic Observation
Alumina Coating falls off when touched or when placed on a table top to rest there.
Zirconia toughened alumina As above.
Yttria stabilized zirconia Coating can be removed from ceramic by scratching with a thumbnail.
MgTTZ Coating has extremely strong holding to ceramic and cannot be removed from ceramic, even with hand tool.

EXAMPLE 2

Trial discs of MgO-TTZ are fully fired, and some are polished to a smooth finish. Samples of the fired, unpolished and unroughened discs, and of the fired, polished discs are coated with CPT as in Example 1. The CPT does not stick nearly well, if it sticks at all, to the unpolished unroughened discs, as it does to all of the polished discs, which is tenaciously.

EXAMPLE 3

Some fired MgO-TTZ discs are polished with diamond dust, and some with alumina, and all are coated with CPT as in Example 1. The coating sticks tenaciously in all cases.

EXAMPLE 4

About 70~80 MgO-TTZ discs are polished with diamond dust with belt and vibratory polishing. The discs are coated with CPT as in Example 1. The coating sticks tenaciously in all cases.

CONCLUSION TO THE INVENTION

The present invention is thus provided. Various feature(s), part(s), step(s), subcombination(s) and/or combination(s) can be practiced with or without reference to other feature(s), part(s), step(s), subcombination(s) and/or combination(s) in the practice of the invention, and numerous adaptations and modifications can be effected within its spirit, the literal claim scope of which is particularly pointed out as follows:

I claim:

1. An article of manufacture comprising a fired magnesium oxide stabilized zirconia ceramic body having a highly smooth surface of said zirconia, which is at least as smooth as an about 2-Ra micro-inch finish; and, directly on at least part of said highly smooth surface, a coating of a metal or a metal alloy, wherein said metal or metal alloy coating is from a metal other than tantalum or a metal alloy other than of tantalum, wherein said coating is at least about 0.015 of an inch thick and resists being pulled or sheared off the magnesium oxide stabilized zirconia ceramic body to a value of about 2,000 pounds or more of force.

2. The article of claim 1, wherein the ceramic body is a magnesium oxide stabilized transformation toughened zirconia.

3. The article of claim 2, wherein said coating is titanium or a metal alloy with titanium.

4. The article of claim 1, wherein said coating is titanium or a metal alloy with titanium.

5. The article of claim 1, which is an orthopedic implant or component for an orthopedic implant where the fired magnesium oxide stabilized zirconia ceramic body embraces a body for the implant or component having the aforesaid surface; and, on at least part of the surface, said coating.

6. The article of claim 5, wherein the orthopedic implant or component is a load bearing implant or component for a load bearing implant having an articular surface and a nonarticular surface, where at least part of said coating is a porous coating, which is on at least part of the nonarticular surface.

7. The article of claim 6, wherein the load bearing implant or component for a load bearing implant is selected from the group consisting of a bicompartmental femoral component for a knee, a unicompartmental femoral component for a knee, a tibial component for a knee, a patellofemoral implant, an acetabular cup, a glenoid cup, a great toe implant, a temporal mandibular joint, a talus cap for an ankle implant or ensemble, and a tibial component for an ankle implant or ensemble.

8. The article of claim 7, wherein the ceramic body is a magnesium oxide stabilized transformation toughened zirconia.

9. The article of claim 8, wherein said coating is titanium or a metal alloy with titanium.

10. The article of claim 9, wherein said coating is a commercially pure titanium.

11. The article of claim 6, wherein the ceramic body is a magnesium oxide stabilized transformation toughened zirconia.

12. The article of claim 11, wherein said coating is titanium or a metal alloy with titanium.

13. The article of claim 12, wherein said coating is a commercially pure titanium.

14. The article of claim 5, wherein the ceramic body is a magnesium oxide stabilized transformation toughened zirconia.

15. The article of claim 14, wherein said coating is titanium or a metal alloy with titanium.

16. The article of claim 15, wherein said coating is a commercially pure titanium.

17. The article of claim 1, which is a tool.

18. The article of claim 1, wherein said coating resists being pulled or sheared off the magnesium oxide stabilized zirconia ceramic body to a value of about 3,000 pounds or more of force.

19. The article of claim 1, wherein said coating resists being pulled or sheared off the magnesium oxide stabilized zirconia ceramic body to a value of about 5,000 pounds or more of force.

20. The article of claim 1, wherein said coating resists being pulled or sheared off the magnesium oxide stabilized zirconia ceramic body to a value of about 7,000 pounds or more of force.

\* \* \* \* \*